United States Patent
Nashner (10) Patent No.: US 7,195,355 B2
(45) Date of Patent: Mar. 27, 2007

(54) ISOLATING AND QUANTIFYING FUNCTIONAL IMPAIRMENTS OF THE GAZE STABILIZATION SYSTEM

(75) Inventor: Lewis M. Nashner, Portland, OR (US)

(73) Assignee: NeuroCom International, Inc., Clackamas, OR (US)

( * ) Notice: Subject to any disclaimer, the term of this patent is extended or adjusted under 35 U.S.C. 154(b) by 83 days.

(21) Appl. No.: 11/117,714

(22) Filed: Apr. 28, 2005

(65) Prior Publication Data

US 2005/0243277 A1 Nov. 3, 2005

Related U.S. Application Data

(60) Provisional application No. 60/565,905, filed on Apr. 28, 2004.

(51) Int. Cl.
*A61B 3/028* (2006.01)
*A61B 3/032* (2006.01)
*A61B 3/113* (2006.01)

(52) U.S. Cl. .................. 351/246; 351/209; 351/222; 351/239

(58) Field of Classification Search ............. 351/209, 351/222, 239, 246; 600/558
See application file for complete search history.

(56) References Cited

U.S. PATENT DOCUMENTS

| | | | |
|---|---|---|---|
| 4,034,401 A * | 7/1977 | Mann | 348/115 |
| 4,738,269 A | 4/1988 | Nashner | |
| 4,807,986 A * | 2/1989 | Wasserman | 351/200 |
| 4,830,024 A | 5/1989 | Nashner | |
| 4,838,681 A * | 6/1989 | Pavlidis | 351/210 |
| 5,052,406 A | 10/1991 | Nashner | |
| 5,180,907 A * | 1/1993 | Udden et al. | 250/205 |
| 5,303,715 A | 4/1994 | Nashner et al. | |
| 5,474,087 A | 12/1995 | Nashner | |
| 5,478,239 A * | 12/1995 | Fuerst et al. | 473/438 |
| 5,697,791 A | 12/1997 | Nashner et al. | |
| 5,942,954 A | 8/1999 | Galiana et al. | |
| 5,953,102 A * | 9/1999 | Berry | 351/247 |
| 6,106,119 A * | 8/2000 | Edwards | 351/209 |
| 6,796,947 B2 * | 9/2004 | Watt et al. | 600/552 |

(Continued)

OTHER PUBLICATIONS

"Disorders of the Vestibular System" edited by Robert W. Baloh and G. Michael Halmagyi, Chapters 3 and 6, Oxford University Press, New York, 1996.

(Continued)

*Primary Examiner*—Charles A Marmor, II
*Assistant Examiner*—John R Sanders
(74) *Attorney, Agent, or Firm*—Bromberg & Sunstein LLP (57) ABSTRACT

A method for isolating and quantifying impairments of a subject's gaze stabilization system is provided. A subject's static visual acuity is measured to arrive at an assessment. The subject's visual acuity is then measured when the subject's head is moving and a display object is fixed to arrive at a first dynamic measurement. The subject's visual acuity is also measured when the subject's head is fixed and the display object is moving to arrive at a second dynamic measurement. The assessment and the first and second dynamic measurements are then used to determine an impairment of the subject's gaze stabilization system.

30 Claims, 4 Drawing Sheets

U.S. PATENT DOCUMENTS

| | | | |
|---|---|---|---|
| 6,997,556 B2 * | 2/2006 | Pfleger | 351/246 |
| 2002/0011250 A1 * | 1/2002 | Stewart et al. | 128/898 |
| 2002/0151818 A1 | 10/2002 | Watts et al. | |
| 2003/0086061 A1 | 5/2003 | Pfleger | |

OTHER PUBLICATIONS

Nashner et al, "Head-trunk movement coordination in the standing posture," Chapter 21, Vestibulospinal Control of Posture and Locomotion, Progress in Brain Research, vol. 76. Amsderdam Elsevier Science Publishers, pp. 243-251, 1988.

Shepard et al., "Rotational Chair Testing" in Practical Management of the Balance Disorder Patient, Chapter 6, Singular Publishing Group, Inc., San Diego, p. 221, 1996.

Shepard et al., "Electronystagmography Evaluation" in Practical Management of the Balance Disorder Patient, Chapter 4, Singular Publishing Group, Inc., San Diego, p. 221, 1996.

Demer et al., "Dynamic visual acuity: a test for oscillopsia and vestibule-ocular reflex function," American Journal of Otology, vol. 15 pp. 340-347, 1994.

Herdman et al., "Computerized dynamic visual acuity test in the assessment of vestibular deficits," American Journal of Otology vol. 19, pp. 790-796, 1998.

Koles et al., "The relationship between body sway and foot pressure in normal man," Journal of Medical Engineering and Technology, vol. 4, pp. 279-285, 1980.

International Search Report dated Aug. 30, 2006.

* cited by examiner

ISOLATING AND QUANTIFYING FUNCTIONAL IMPAIRMENTS OF THE GAZE STABILIZATION SYSTEM

The present application claims priority from U.S. Provisional Application No. 60/565,905, filed Apr. 28, 2004, which is hereby incorporated herein, in its entirety, by reference.

TECHNICAL FIELD

The present invention relates to gaze stabilization and, more particularly to isolating and quantifying impairments of a subject's gaze stabilization system.

BACKGROUND ART

In subjects with chronic balance disorders, approaches to medical treatment based on drugs and surgery can be effective in stabilizing the pathological processes that cause the disorders. In such subjects, these approaches can sometimes stabilize but seldom fully resolve the underlying pathological manifestations of the balance problem. Once the underlying pathological processes are medically stable however, rehabilitation exercises frequently prove effective in reducing many of the disabling symptoms and functional problems associated with chronic balance disorders. Hence, effective treatment of chronic balance disorders typically employs combinations of medical and rehabilitation exercise treatments.

In selecting medical treatments most likely to stabilize underlying pathological processes, clinicians first determine the location, nature, and extent of the underlying pathological process. To make pathological determinations, clinicians typically rely on the results of the subject history and physical examination to develop diagnostic hypotheses, and then use site-of-lesion laboratory tests to confirm or rule out their hypotheses. In designing effective rehabilitation exercise programs, in contrast, clinicians require additional knowledge of the subject's functional impairments and adaptive response capabilities. For this reason, objective tests that isolate and quantify the functional impairments associated with balance disorders complement the information provided by site-of-lesion tests and complete the clinical information necessary for effective treatment planning and outcome documentation.

To develop methods and devices for isolating and quantifying functional impairments of the balance system, it is first necessary to understand the functional organization of the balance system. The balance system includes a number of processes that can be grouped into distinct but interdependent systems—one responsible for gaze stabilization and the other responsible for postural stabilization. The gaze stabilization system maintains the gaze direction of the eyes relative to surrounding visual targets as the subject actively moves within his or her environment. Stabilizing the direction of gaze while a person moves maintains their visual acuity during activities involving active head and body movements. When individuals with impaired gaze stabilization participate in activities involving self-motion and moving objects in the surrounds, moving objects can appear blurred while stationary objects can become blurry and sometimes appear to be in motion.

A detailed discussion of gaze stabilization can be found in "Disorders of the Vestibular System" edited by Robert W. Baloh and G. Michael Halmagyi and published by Oxford University Press, New York, in 1996 (Chapters 3 *How Does the Vestibulo-ocular Reflex Work?*, and Chapter 6, *How Does the Visual System Interact with the Vestibulo-ocular Reflex?* both of which are hereby incorporated herein by reference). In summary, the gaze stabilization system directs the eyes towards visual objects in the surround through the cooperative interactions of four movement subsystems:

1) The vestibulo-ocular reflex (VOR) system. The VOR is a fast acting system that relies on sensory inputs from angular velocity sensors within the vestibular system (called semicircular canals) to reflexively rotate the eyes in directions that are equal and opposite the rotations of the head. These eye movements are mediated by relatively direct brainstem pathways linking receptors of the semicircular canals with the eye muscles. Hence, VOR movements are fast and able to compensate head movements at frequencies up to 2.0 Hz without needing visual information about object position. Because VOR movements are controlled by inner ear head velocity sensors, they are ineffective at rotation frequencies below 0.1 Hz. Furthermore, the VOR is most accurate in opposing head movements about the yaw axis, i.e. head movements to the left and right of center in the horizontal plane, and is less accurate for pitch axis movements, i.e. up and down movements in the vertical plane.

2) The smooth pursuit eye movement system. The smooth pursuit eye movement system enables individuals to direct their gaze to discrete moving objects within their visual surround. This gaze stabilization system relies on visual position information from the selected object. It is significantly slower than the VOR, because the visual feedback information is mediated by complex pathways involving image processing within the visual cortex. In contrast to the VOR, the smooth pursuit system is effective at the lowest frequencies of head movement and is equally accurate for movements in all directions.

3) The saccadic movement system. The saccadic movement system generates rapid "catch-up" eye movements directed from any given gaze position to the direction of a selected discrete object within an individual's visual surround. Like smooth pursuit movements, saccadic movements require visual position information relative to the selected visual object. In contrast to smooth pursuit movements, saccadic movements are faster acting, but they are limited to discontinuous direction changes rather than smooth continuously controlled movements.

4) The optokinetic movement system. The optokinetic movement system generates smooth eye movements in the direction of continuous, large field motions of the visual surround. Smooth optokinetic movements in the direction of the large field motion are interposed between brief saccadic movements that return the gaze direction back to the original position. In contrast to the smooth pursuit system, optokinetic movements require large fields of continuous, uniform visual surround motion. In the absence of a discrete target, the optokinetic system can stabilize the eyes on a large field visual surround for brief intervals of time. When a discrete target and its surrounding background field are moving together, the optokinetic system can assist the smooth pursuit system in tracking the discrete object. On the other hand, when a discrete target and its large field background move differently, the smooth pursuit and optokinetic systems can potentially interfere with one another.

In addition to the above four eye movement control systems, there are reflexive, automatic and voluntary motor systems for moving the head relative to the body. These movement systems provide additional assistance in maintaining the stability of gaze on visual objects within the surrounds. Automatic compensatory head movements that accompany automatic stabilizing postural movements during upright standing are examples of head movements that assist in gaze stabilization. As described by Nashner L M, Shupert C L, Horak F B. *Head-trunk movement coordination in the standing posture* in Chapter 21 of Pompeiano O, Allum J H J, eds. (1988) Vestibulospinal Control of Posture and Locomotion, Progress in Brain Research, Vol 76. Amsderdam Elsevier Science Publishers, pp. 243–251 (which is hereby incorporated by reference), automatic postural responses that sway the body backwards and forwards about the ankles and hips are coordinated with automatic head-neck movements that pitch the head in the opposing direction, thereby helping to maintain the angular orientation of the head relative to the visual surrounds.

During daily life activities, cooperative interactions among the VOR, smooth pursuit, saccadic, and optokinetic eye movement systems, as well as between the postural and head-neck movement systems, allow individuals to maintain their direction of gaze on selected visual objects in their surrounds while performing motor tasks under a wide variety of conditions. When the head is moving and the selected visual target is fixed, the VOR system stabilizes the direction of gaze during more rapid movements while the smooth pursuit system, assisted by the optokinetic system under some conditions, provides gaze stability relative to the slower head movements. When the head is fixed and objects in the visual surround are moving, the smooth pursuit system, again assisted by the optokinetic system under some conditions, stabilizes gaze on objects that are moving slowly. When surrounding objects move more rapidly, the smooth pursuit system cannot maintain gaze stability, and "catch-up" saccadic eye movements are used to re-stabilize the gaze. When the body sways during standing, moves up and down, moves from side to side, and/or tilts forward and backward during locomotion, coordination of postural and head-neck movements help maintain the angular orientation of the head relative to the visual surrounds.

When individuals suffer pathological changes in one or more of the four eye movement systems, changes in the adaptive interactions among the four systems may compensate for some of the resulting gaze problems, while other gaze stabilization problems may persist regardless of any adaptive changes. Some subjects with defects in the VOR system, for example, attempt to deliberately limit their activities to slower head movements and substitute smooth pursuit movements to stabilize their gaze on fixed objects. When forced to make more rapid head movements, these individuals may use catch-up saccades that, at best, provide only intermittent gaze stability.

To effectively plan courses of treatment for individuals with impaired gaze stability, the clinical evaluation should provide the following: 1) isolation and quantification of the impairments to gaze stabilization; 2) identification of impairments that can be ameliorated or eliminated by medical and/or rehabilitation therapies; and 3) identification of adaptive strategies that will result in the best visual acuity function relative to the subject's lifestyle demands. Due to wide variations in the relations between pathological and functional mechanisms among subjects, clinicians desiring to improve a subject's gaze control function require information not only of the underlying pathologies but also of the impairments affecting the four control systems and their adaptive interactions.

Because systems for maintaining postural and gaze stability share visual, vestibular, and proprioceptive sources of orientation information and the systems for controlling body and head-neck stabilizing movements are coordinated, subjects with pathological changes in systems for maintaining postural stability may also experience problems with gaze stability and visual acuity. Therefore, to effectively plan courses of treatment for individuals with impaired gaze stability, it is frequently necessary to isolate and quantify additional impairment information related to interactions among the systems for postural and head-neck stabilization.

There are observational and computerized objective tests within the prior art for evaluating individual components the gaze stabilization system and for testing an individual's visual acuity while moving:

1) The VOR System: Rotary chair systems manufactured by several companies, are considered standard methods for quantifying the physiological characteristics of the VOR system. A subject is harnessed into a chair with his or her head fixed and the room darkened. The chair is rotated about a fixed vertical axis under computer control while movement responses of the eyes are recorded using either electrical or infrared optical methods. The computer controls the frequency the chair rotations, records the resulting eye movements, and then correlates the two quantities to determine the gain, phase, and directional preponderance relationships between head and eye movements across a spectrum of frequencies. A detailed description of rotational chair testing of the VOR, including additional scientific and clinical references, can be found in Chapter 6 entitled "Rotational Chair Testing" in: *Practical Management of the Balance Disorder Patient* by Neil T. Shepard and Steven A. Telian (1996) Singular Publishing Group, Inc. San Diego pp. 221 (which is incorporated herein by reference).

2) Saccadic System. Eye movement systems manufactured by several companies including ICS Medical of Shaumberg, Ill., and Micromedical Systems of Springfiled Ill. quantify the physiological characteristics of the saccadic eye movement system. A subject sits in a chair and views a light bar display on which discrete targets are displayed under computer control while his or her eye movements are measured using either electrical or infrared optical methods and recorded by the computer. The subject is instructed to track targets that jump suddenly from one position to another on the light bar display. The computer then correlates the movements of the subject's eyes relative to the timing, direction, and amplitude of target movements to quantify the latency, velocity, and accuracy of the resulting saccadic eye movements. A detailed description of saccadic eye movement testing, including additional scientific and clinical references, can be found in Chapter 4 entitled "Electronystagmography Evaluation" in: *Practical Management of the Balance Disorder Patient* by Neil T. Shepard and Steven A. Telian (1996) Singular Publishing Group, Inc. San Diego pp. 221 (which is incorporated herein by reference).

3) Smooth Pursuit System. This movement system is typically tested using either observational methods or recorded eye movements. During observational testing, a subject follows the clinician's finger while the clinician observes the eye movements. The clinician observes whether the subject's eyes move smoothly and in conjunction (together), in a series of small jerks, or disconjugately. Jerky and/or disconjugate eye movements are indicative of failure of the smooth pursuit system. Alternatively, the subject's pursuit eye movements may be electrically or optically recorded and the degree of smoothness evaluated by analyzing the smooth pursuit "velocity gain", the speed of the eye movement compared to the speed of the target movement, and by visually inspecting the recorded eye movement traces for evidence of small movement jerks. A detailed description of smooth pursuit eye movement testing, including additional scientific and clinical references, can be found in Chapter 4 entitled "Electronystagmography Evaluation" in: *Practical Management of the Balance Disorder Patient* by Neil T. Shepard and Steven A. Telian (1996) Singular Publishing Group, Inc. San Diego pp. 221 (which is incorporated herein by reference).

4) Optokinetic System. The optokinetic system can also be tested observationally or with recorded eye movements. During either type of testing, a subject views a large field surface with high contrast, alternating stripes that move continuously in a direction perpendicular to the orientation of the strips. The intensity of the subject's optokinetic eye movements relative to the velocity of the large field surface movement, slow in the direction of stripe movement and rapid in the opposite direction, are then documented.

5) Dynamic Visual Acuity. Differences in a subject's visual acuity with the head fixed and head moving can be quantified using observational methods or computerized devices manufactured by several companies including NeuroCom International, Inc. of Clackamas, Ore., and Micromedial of Springfield, Ill. Observational tests of dynamic visual acuity (DVA) are based on the standard Snellen eye chart. As described by Demer J L, Honrubia V, Baloh R W (1994) "*Dynamic visual acuity: a test for oscillopsia and vestibule-ocular reflex function*" American Journal of Otology 15: 340–347 (herein incorporated by reference), visual acuity is assessed, first with the head fixed and second with the subject moving the head back and forth at a pace instructed by the administrator of the test. By observing the subject, the test administrator verifies that the subject continues moving the head while reading the Snellen chart. The DVA results are reported as the number of Snellen lines of acuity decrement observed during the head moving as compared to head fixed conditions. Another form of eye chart that may be employed is the so-called "Tumpling E". In accordance with tests using the Tumpling E, a subject views a letter "E" of a specified optotype size and orientation and is asked to correctly identify the orientation of the "E" (up, down, left, right).

The observational DVA test has several problems that limit the value of the information in discriminating among the various causes for loss of gaze stability: (1 results are approximate, because the administrator can only estimate the velocity of the subject's head movements; and (2 some subjects can compensate for losses within the VOR stabilization system by very briefly slowing their head movements for small fractions of a second and using catch-up saccadic movements to stabilize gaze on the chart.

In computerized versions of the dynamic visual acuity test, visual images are generated and displayed by computer, subjects wear sensors on the head that quantify head movement velocities, and the computer receives the head movement information and controls the presentation times of visual images such that they appear only when the head is moving in accordance with instructions. These methods prevent subjects from compensating with catch-up saccadic movements and also allow precise specification and verification of the head movement velocity. A description of computerized dynamic visual acuity testing can be found in Herdman, S, Tusa R, Blatt P, Suzuki A, Venuto P J, Robert D (1998) "Computerized dynamic visual acuity test in the assessment of vestibular deficits." American Journal of Otology 19:790–796 (which is hereby incorporated herein by reference).

There are also observational and computerized objective tests for evaluating individual components of postural stability while an individual stands freely and/or walks:

1) One commonly used observational clinical test for assessing an individual's postural stability was described by Koles Z J, Castelein R D (1980) "*The relationship between body sway and foot pressure in normal man*" Journal of Medical Engineering and Technology 4: 279–285 (which is also incorporated herein by reference).

2) A number of manufacturers including NeuroCom International, Inc. of Clackamas, Ore., and Micromedical Technologies of Springfield, Ill., manufacture simple postural stability assessment devices utilizing fixed forceplate measuring devices, as well as forceplates suspended on compliant devices, linked to computers. These devices quantify an individual's postural sway while standing quietly and during attempts to shift the body weight.

3) In previously issued patents related to sensory integration and movement coordination analysis series, apparatus and methods for characterizing gait, etc., (including U.S. Pat. Nos. 4,738,269, 4,830,024, 5,052,406, 5,303,715, 5,474,087 and 5,697,791—all incorporated herein by reference) the present inventor has described methods and devices for measuring the postural stability of individuals standing and walking while subjected to perturbations generated by controlled movements of the support surface. Some of these methods and devices have been incorporated into the EquiTest® system manufactured and marketed by NeuroCom International, Inc. of Clackamas, Ore.

It is generally understood that the vestibular function and eye movement control information provided by rotary chair, smooth pursuit, saccadic, and optokinetic tests, as well as other "site of lesion" otologic and neurological tests of vestibular and motor system physiological functions do not correlate well with the symptoms and functional impairments experienced during daily life activities by subjects with balance system problems. This is because gaze and postural stabilization systems are highly adaptive, and individual subjects with similar pathologies use their residual VOR, smooth pursuit, saccadic, optokinetic, and postural stability capabilities differently, resulting in different symptoms and functional problems. The DVA test, in contrast, does quantify how well a subject can accurately perceive fixed visual objects while moving the head. For reasons described above, however, the DVA test alone does not isolate and quantify impairments related to gaze stabilization while individuals attempt to view: (1) fixed visual targets while moving the head, (2) moving targets with the head fixed, (3) fixed or moving targets while maintaining free standing and walking balance, and (4) combinations of these task conditions.

During daily life activities, such as driving a car or participating in recreational sports activities, individuals are frequently required to observe stationary and moving visual objects while they themselves are actively moving. The ability to differentiate among a variety of impairments contributing to poor gaze stability and visual acuity during these types of daily life activities would have significant clinical value. In the majority of subjects with balance system problems affecting gaze stability, pharmacological and surgical treatments designed to stabilize or reduce the impact of disease processes are guided by information provided by physiological "site of lesion" tests. While medical treatments can sometimes stabilize the underlying patho-physiological processes and thereby slow the progression of disease, such treatments seldom resolve the underlying pathology or eliminate a subject's functional gaze and postural stability problems. Rehabilitation treatments, in contrast, can substantially improve gaze and postural stability functions and reduce adverse symptoms in a majority of subjects. In contrast to medical treatment planning, however, isolating and quantifying impairments provides the information necessary to focus training exercises on those impairments having the greatest negative impact on the subject's daily life activities. Impairment information also provides objective benchmark against which treatment results can be documented.

Embodiments of the present invention relate to new methods and devices for isolating and quantifying functional impairments among the VOR, smooth pursuit, saccadic, optokinetic eye movement, postural stability systems, and their adaptive interactions.

SUMMARY OF THE INVENTION

In a first embodiment of the invention there is provided a method for isolating and quantifying impairments of a subject's gaze stabilization system. The method includes measuring the subject's static visual acuity to arrive at an assessment, measuring the subject's visual acuity when the subject's head is moving and a display object is fixed to arrive at a first dynamic measurement and measuring the subject's visual acuity when the subject's head is fixed and the display object is moving to arrive at a second dynamic measurement. The assessment and the first and second dynamic measurements are used to determine an impairment of the subject's gaze stabilization system.

In accordance with a related embodiment, measuring the subject's static visual acuity to arrive at an assessment may include using the assessment to set parameters for a performance of a task by the subject. In accordance with another related embodiment, the method may further include measuring the subject's visual acuity when the subject's head is fixed and the display object is discontinuously moving to arrive at a third dynamic measurement and using the assessment and the first, second and third dynamic measurements to determine impairment of the subject's gaze stabilization system. In accordance with a further related embodiment, the method may also include measuring the subject's visual acuity when the subject's head is fixed, the display object is moving, and a patterned large field background is moving to arrive at a fourth dynamic measurement to determine impairment of the subject's gaze stabilization system.

In accordance with other related embodiments, assessing the subject's static visual acuity may include determining a smallest object that the subject can identify during a plurality of trials and/or measuring the subject's visual acuity when the subject's head is moving and the display object is fixed may include fixing the size of the display object in relation to the subject's static visual acuity, fixing the duration that the display object is displayed to between 40 and 100 milliseconds (or, in accordance with one embodiment for approximately 75 milliseconds), and determining the maximum head movement velocity during which the subject can correctly identify the display object over a plurality of trials. Additionally, measuring the subject's visual acuity when the subject's head is fixed and the display object is continuously moving may include fixing the size of the display object in relation to the subject's static visual acuity, fixing the duration that the display object is displayed to between 40 and 100 milliseconds (or, in accordance with one embodiment, for approximately 75 milliseconds), and determining the maximum display object movement velocity during which the subject can correctly identify the display object over a plurality of trials. Similarly, measuring the subject's visual acuity when the subject's head is fixed and the display object is continuously moving may include displaying a patterned large field background and moving the patterned large field background.

In accordance with still other related embodiments, measuring the subject's visual acuity when the subject's head is fixed and the display object is discontinuously moving may include fixing the size of the display object in relation to the subject's static visual acuity, fixing the duration that the display object is displayed to about 90 milliseconds, causing the subject to direct gaze towards a central marker for between 40 and 100 milliseconds (or in accordance with one embodiment, for approximately 75 milliseconds), causing the display object to appear at a predetermined location relative to the central marker, and determining the maximum distance from the central marker during which the subject can correctly identify the display object over a plurality of trials. Further, causing the display object to appear at a predetermined location relative to the central marker may include causing the display object to appear at a fixed distance from the central marker. Additionally, causing the display object to appear at a predetermined location relative to the central marker may include causing the display object to appear at various directions from the central marker. In accordance a further related embodiment, measuring the subject's static visual acuity may include using a Snellen and/or Tumpling E eye chart.

In accordance with yet other related embodiments, the method may include directing the subject to perform at least one free standing balance task while the subject's visual acuity is measured. Directing the subject to perform at least one free standing balance task may include directing the subject to stand on at least one surface which moves in relation to display of the display object. The method may also include the process of moving a patterned large field background in relation to the movement of the surface. The surface may move continuously or discontinuously in relation to display of the display object. Further, the surface may be a force plate or a treadmill, and the velocity associated with the treadmill may be constant or the velocity may be caused to vary. Additionally, directing the subject to perform at least one free standing balance task may include directing the subject to perform at least one free standing balance task while surrounded by a visual surround.

In accordance with another embodiment of the invention, a method for isolating and quantifying impairments of a subject's gaze stabilization system includes assessing the subject's static visual acuity, measuring at least two aspects of the subject's dynamic visual acuity and calculating a first quantity related to both the subject's static visual acuity and a first aspect of the subject's dynamic visual acuity. The first quantity is compared with a normative value similarly derived from a population of individuals free of gaze stabilization impairments, and an impairment of the subject's gaze stabilization system is determined when the first quantity varies from the normative value by more than one standard deviation. In accordance with a related embodiment, measuring aspects of the subject's dynamic visual acuity may include measuring aspects of the subject's dynamic visual acuity related to two or more of: the subject's vestibule-ocular reflex system, the subject's smooth pursuit eye movement system, the subject's optokinetic eye movement system, and/or the subject's saccadic movement system. In accordance with another related embodiment, the method may also include calculating a second quantity related to the subject's static visual acuity and a second aspect of the subject's dynamic visual acuity, comparing the second quantity with a normative value similarly derived from a population of individuals free of gaze stabilization impairments, and determining a second impairment of the subject's gaze stabilization system when the third quantity varies from the normative value by more than one standard deviation.

In accordance with a further embodiment of the invention, a method for isolating and quantifying impairments of a subject's gaze stabilization system includes assessing the subject's static visual acuity, measuring the subject's visual acuity when the subject's head is moving and a display object is fixed to determine a first relationship to the subject's static visual acuity, measuring the subject's visual acuity when the subject's head is fixed and the display object is continuously moving to determine a second relationship to the subject's static visual acuity, measuring the subject's visual acuity when the subject's head is fixed and the display object is discontinuously moving to determine a third relationship to the subject's static visual acuity and/or measuring the subject's visual acuity when the subject's head is fixed, the display object is continuously moving, and a patterned large field background is continuously moving to determine a fourth relationship to the subject's static visual acuity. The extent to which impairments of the subject's gaze stabilization system reduce the subject's ability to perceive objects is determined based on the first, second, third, and fourth relationships.

In accordance with yet another embodiment of the invention, a method for isolating and quantifying impairments of a subject's gaze stabilization system includes measuring the subject's static visual acuity to arrive at an assessment, measuring the subject's visual acuity when the subject is standing on a continuously moving support surface, the subject's head is moving and a display object is fixed to arrive at a first dynamic measurement, and/or measuring the subject's visual acuity when the subject is standing on a continuously moving support surface, the subject's head is fixed and the display object is moving to arrive at a second dynamic measurement. The assessment and the first and second dynamic measurements are used to determine an impairment of the subject's gaze stabilization system.

In accordance with yet a further embodiment of the invention, a method for isolating and quantifying impairments of a subject's gaze stabilization system includes measuring the subject's static visual acuity to arrive at an assessment, measuring the subject's visual acuity when the subject is standing on a support surface that is discontinuously moving, the subject's head is moving and a display object is fixed to arrive at a first dynamic measurement, and measuring the subject's visual acuity when the subjects is standing on a support surface that is discontinuously moving, the subject's head is fixed and the display object is moving to arrive at a second dynamic measurement. The assessment and the first and second dynamic measurements are used to determine an impairment of the subject's gaze stabilization system.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

The present invention involves new methods and devices for isolating and quantifying functional impairments of the gaze stabilization system that negatively impact a subject's ability to maintain their visual orientation and acuity while the subject and/or surrounding visual objects are moving. This is accomplished by combining assessment information derived from three test procedures: (1) at least one measure of an subject's static visual acuity, (2) one or more measures of an subject's visual acuity while the head moves in accordance with a prescribed protocol and the surrounding visual objects remain stationary, and (3) one or more measures of an subject's visual acuity while the head is stationary and surrounding objects move in accordance with a prescribed protocol. Additional embodiments of the invention combine one or more of the above three procedures with additional procedures in which the subject stands freely in the presence of perturbations to postural stability or walks freely.

Further embodiments of the invention pertain to computational methods and devices that differentiate and quantify impairments affecting the gaze stabilization system by combining visual acuity information, derived from the above three procedures and displaying the combined results in graphical or numerical formats. In embodiments that combine the above three procedures with additional postural stability procedures, the graphical and numerical results combine visual acuity and postural stability information.

Figure 1:
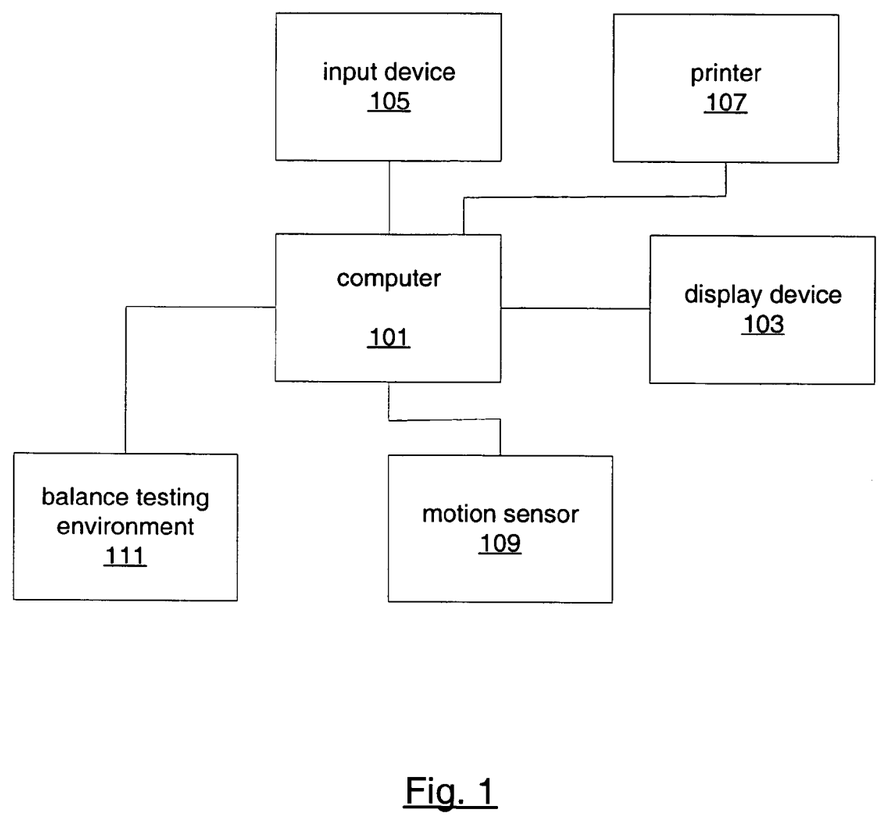
FIG. 1 is a block diagram illustrating a system which may be used to measure aspects of a subject's gaze stabilization system in accordance with one embodiment of the invention.

FIG. 1 is a block diagram illustrating a system which may be used to measure aspects of a subject's gaze stabilization system in accordance with one embodiment of the invention. The system includes a computer 101, which may include a dedicated microprocessor, personal computer, server or other computing device. A display 103 may be in communication with the computer 101, as may be an input device 105 (such as a mouse, keyboard, voice activated input system, light activated input system or touch activated input system). The system may also include a printer 107 or other output device in communication with the computer 101. A motion sensor 109, such as a 3-axis, integrating gyro mounted on a headband or other motion sesnsor, may be used to monitor velocity and direction of head movements of a subject. One example of a system which includes such a headband is the InVision™ system manufactured by NeuroCom International, Inc. of Clackamas, Ore.

The system may further include a balance testing environment 111, which may include a stationary forceplate, a cushion, or a moveable treadmill in communication with the computer 101. Examples of systems that include forceplates include the BalanceMaster®, the VSR™, the PRO Balance-Master®, and the SMART BalanceMaster® all manufactured by Neurocom International, Inc. of Clackamas, Ore. Such a system may include a visual surround or other moveable environment, such as the visual surround included in the EquiTest® or SMART EquiTest® systems manufactured by Neurocom International, Inc. of Clackamas, Ore.

Figure 2:
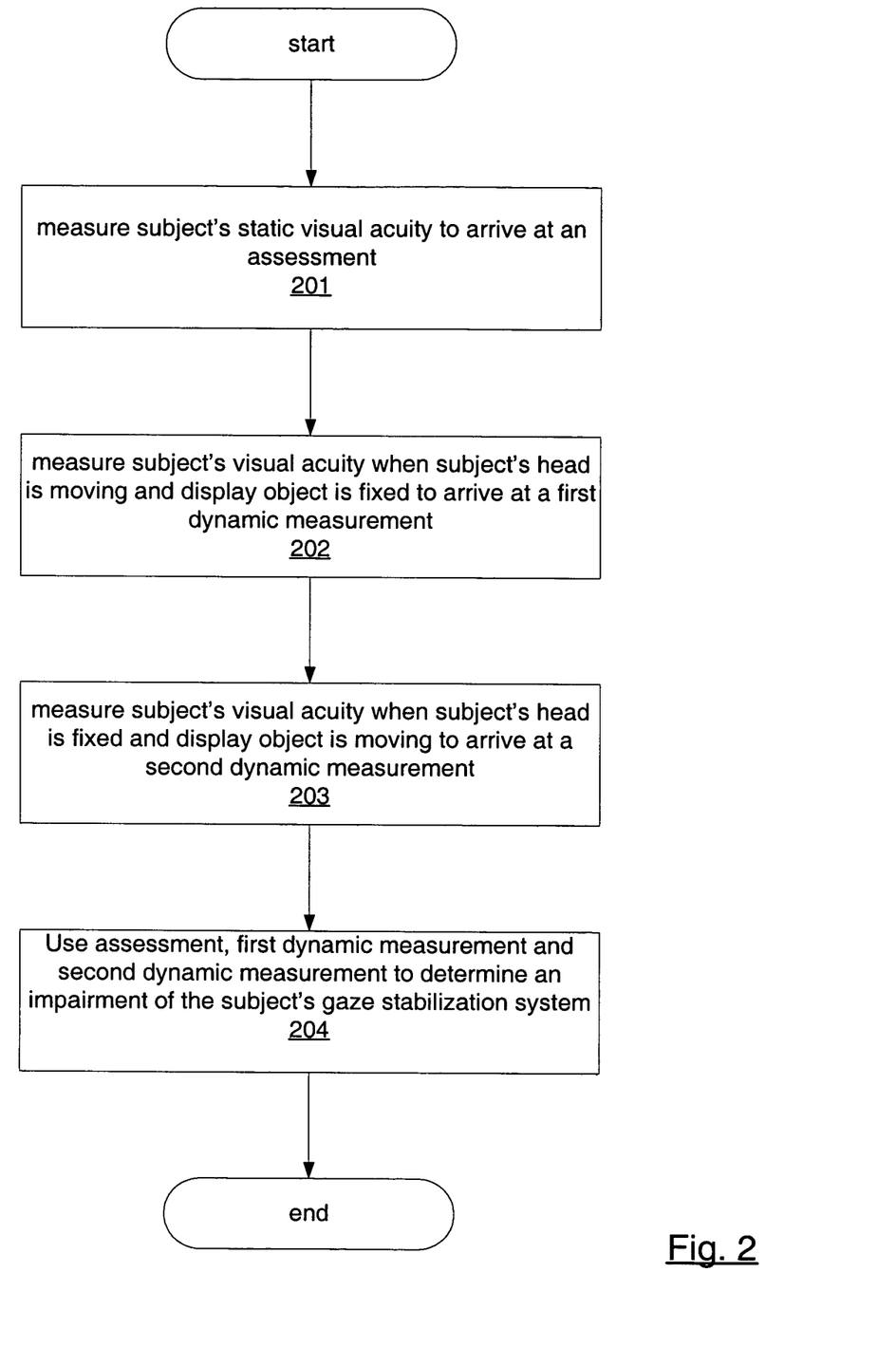
FIG. 2 is flow chart illustrating a method for isolating and quantifying impairments of a subject's gaze stabilization system in accordance with another embodiment of the invention.

FIG. 2 is flow chart illustrating a method for isolating and quantifying impairments of a subject's gaze stabilization system in accordance with an embodiment of the invention. In accordance with this embodiment, the subject's static visual acuity is measured 201 to arrive at an assessment. The subject's static visual acuity may be assessed using any one of a variety of standardized and clinically accepted means; including, a Snellen eye chart, Tumpling E chart, or a variety of commercially available mechanized and computerized versions of the eye chart acuity test. Micromedical Technologies of Springfield, Ill., and NeuroCom International, Inc. of Clackamas, Ore., are two companies that manufacture computerized systems for measuring static visual acuity. Further, measuring the subject's static visual acuity to arrive at an assessment may include using the assessment to set parameters for a performance of a task by the subject as will be described in more detail below.

In process 202, the subject's visual acuity is measured when the subject's head is moving and a display object is fixed to arrive at a first dynamic measurement. For example, a sensor, such as sensor 109, capable of measuring one or more quantities related to movement may be attached to the subject's head and the resulting head movement quantities transmitted to a computer, such as computer 101, which may be in communication with a display device, such as display 103. The computer may be capable of controlling the time, position, size, shape, orientation, and the large field background of one or more visual "display objects". Two examples of embodiment means for displaying an object are a CRT/LCD video monitor and a film/LCD projector projecting onto a reflective screen. Objects displayed by either of these preferred or other display means include but are not limited to letters or common shapes such as circles, rectangles, triangles, stars, equal and plus signs, etc.

In accordance with one protocol which may be followed in accordance with process 202, the subject is instructed to move the head in a prescribed manner and the computer monitors the head movement and identifies one or a plurality of "display time intervals" during which the head is moving in accordance with a "movement criteria." The movement criteria may be a minimum angular velocity of head velocity in a prescribed plane of motion. The computer may then select, at random, a display time interval during which to the display the display object. The subject is then asked to identify one or more attributes of the display object. This protocol may be repeated a number of times and the numbers of correct and incorrect identifications may be recorded by the computer. A change in the task may be triggered by the relative number of correct and incorrect identifications. The protocol may also be repeated with the test made more difficult when the subject makes a minimum of three correct identifications out of five consecutive trials, while the test may be terminated when the number of correct identifications is less than three out of five trials. The test may also be made more difficult by making one or more of the following changes: decreasing the display object size, increasing the display object complexity, reducing or increasing the display object contrast, increasing the movement criteria velocity, changing the movement criteria axis and/or direction, changing the attributes of the large field background, and decreasing the maximum display time interval.

The subject's visual acuity is then measured 203 when the subject's head is fixed and the display object moving in order to arrive at a second dynamic measurement. Again, a sensor capable of measuring angular velocity of movement may be attached to the subject's head and the resulting measures of angular head velocity may be transmitted to a computer. The computer, which may again be in communication with a display device, is capable of controlling the time, position, size, shape, and orientation of visual display objects displayed to the subject.

In accordance with a one protocol which may be followed in accordance with process 203, the subject is instructed to maintain the head in fixed position, the computer displays an initial "fixed position" target, the computer identifies display time intervals during which the subject's head is within the specified "fixed position", with no more than a specified amount or error. In one preferred embodiment, the fixed position criteria is that the subject positions the head to face directly forward with less than a specified number of degrees of position error and a specified number of degrees per second in the rate of change of change of position error. In other preferred embodiments, the subject can be required to direct the head to face in any one of a number of anatomically possible positions, each with specified maximum amounts of position error and/or rates of change in position error. When the subject's head is within the specified fixed position criteria, the computer then selects, at random, a display time interval during which to present the display object as it moves from the holding position to another prescribed position in accordance with a prescribed movement direction and movement velocity, and then disappears. In accordance with some embodiments of the invention, the holding position may be the center of the display area (which may include a screen) and the direction of the display object motion is either to the left, right, up or down. The subject is then asked to identify one or more attributes of the display object. This process may be repeated a prescribed number of times and the numbers of correct and incorrect identifications may be recorded by the computer. A change in the task is triggered by the relative number of correct and incorrect identifications. In accordance with another embodiment, the protocol is repeated with the test made more difficult when the subject makes a minimum of three correct identifications out of five consecutive trials, and the test is terminated when the subject fails to make the minimum three correct identifications. The test may be made more difficult in other embodiments by making one or more of the following changes: decreasing the display object size, increasing the display object complexity, reducing or increasing the display object contrast, increasing the display object movement velocity, changing the display object movement axis and/or direction, changing the attributes of the large field background, moving the large field background either with or independently of the discrete target, and decreasing the maximum display time interval.

In addition to the above measurements, the subject's visual acuity may be measured when the subject's head is fixed and the display object is moving in accordance with discrete or discontinuous movements to arrive at a further dynamic measurement. Once more, a sensor capable of measuring angular velocity of movement may be attached to the subject's head and the resulting measures of angular head velocity are transmitted to a computer. The computer, which may be in communication with a display device, may be capable of controlling the time, position, size, shape, large field background, and orientation of a display object that is displayed to the subject.

For example, in accordance with one protocol, the subject is instructed to maintain the head in fixed position, the computer displays an initial holding position target, the computer identifies display time intervals during which the subject's head meets the position fixed criteria, the computer also selects, at random, a display time interval during which to present the display object for a prescribed interval of time at a prescribed location on the display. The subject is then asked to identify one or more attributes of the display object. This process may be repeated a prescribed number of times and the numbers of correct and incorrect identifications may be recorded by the computer. A change in the task may be triggered by the relative number of correct and incorrect identifications. Once again, this process may be repeated a prescribed number of times. If the subject correctly identifies the attributes of the display object a specified minimum fraction of the trials, the properties of the display object, the display criteria, or both are modified to increase the difficulty of the task and the above process is repeated. The protocol may be repeated with the test made more difficult when the subject makes a minimum of three correct identifications out of five consecutive trials, and the test is terminated when the subject fails to make the minimum three correct identifications. The test may be made more difficult by making one or more of the following changes: decreasing the display object size, increasing the display object complexity, reducing or increasing the display object contrast, increasing the distance between the holding position and the display object position, changing the direction orientation between the holding position and the display position, changing the large field background, and decreasing the maximum display time interval. If the subject fails to correctly identify the prescribed display objects a specified number of times, the test is terminated.

The following calculations may be performed to relate the results of the static visual acuity measure to the dynamic visual acuity measures:

A relation between the first dynamic measurement (i.e., the visual acuity measured when the subject's head is moving and the display object is fixed) and his or her static visual acuity is determined by fixing the size of the display object in relation to the subject's static visual acuity, fixing the duration of time the display object is displayed to allow sufficient time for the subject to perceive the object but insufficient time to perform a catch-up saccadic movement to the object (generally greater than 40 milliseconds and less than 100 milliseconds and, in accordance with one embodiment, for approximately 75 milliseconds), and then determining the maximum head movement velocity during which the subject can correctly identify the object during a minimum three of five consecutive trials. As a specific example, the display object size is twice the size of the smallest object correctly identified during the static visual acuity test. In accordance with some embodiments of the invention, additional maximum head moving/object fixed stabilization scores can be calculated for various dimensions and directions of head movement; for examples, right to left, left to right, up to down, and down to up. In other embodiments, the head movement velocity is fixed and the size of the display object is reduced until the subject fails to correctly identify the display object during a minimum three of five consecutive trials.

A relation between the second dynamic measurement (the subject's visual acuity when the subject's head is fixed and the display object is continuously moving) and his or her static visual acuity is determined by fixing the size of the display object in relation to the subject's static visual acuity, fixing the duration of time the display object is displayed to allow sufficient time for the subject to perceive the object but insufficient time to perform a catch-up saccadic movement to the object (generally greater than 40 milliseconds and less than 100 milliseconds and, in accordance with one embodiment, for approximately 75 milliseconds), and then determining the maximum object movement velocity during which the subject can correctly identify the display object during a minimum three of five consecutive trials. As one example, the display object size is twice the size of the smallest object correctly identified during the static visual acuity test. Additional maximum head fixed/display object continuously moving stabilization scores can be calculated for various dimensions, and directions of object movement; for examples, right to left, left to right, up to down, or down to up. Further, display object movement velocity may be fixed and the size of the display object may be progressively reduced until the subject fails to correctly identify the object during a minimum three of five consecutive trials.

A relation between a third dynamic measurement (the subject's visual acuity when the subject's head is fixed and the display object is continuously moving with a patterned large field background that is itself either fixed or is also moving in relation to the display object movement) and his or her static visual acuity may be determined by fixing the size of the display object in relation to the subject's static visual acuity, specifying the pattern and movement characteristics of the large field background, fixing the duration of time the display object is displayed to allow sufficient time for the subject to perceive the object but insufficient time to perform a catch-up saccadic movement to the object (generally greater than 40 milliseconds and less than 100 milliseconds and, in accordance with one embodiment, for approximately 75 milliseconds), and then determining the maximum object movement velocity during which the subject can correctly identify the display object during a minimum three of five consecutive trials. As one example, the display object size may be twice the size of the smallest object correctly identified during the static visual acuity test and the large field background is a series of black stripes on a white background that move in synchrony with to the display object. Additional maximum head fixed/display object continuously moving stabilization scores may be calculated for various dimensions, and directions of object movement; for examples, right to left, left to right, up to down, or down to up, and for various large field background movements; for examples, a fixed background pattern, a background pattern moving in a different direction than the display object, and a patterned background moving in direct opposition to the display object. Further, display object movement velocity may be fixed and the size of the display object may be progressively reduced until the subject fails to correctly identify the object during a minimum three of five consecutive trials.

A relation between a forth dynamic measurement (the subject's visual acuity when the subject's head is fixed and the display object is discontinuously moving) and his or her static visual acuity may be determined by fixing the size of the display object in relation to the subject's static visual acuity, fixing the duration of time of the display object appearance to 90 milliseconds, instructing the subject to direct gaze towards a focus point (such as a center marker) to allow sufficient time for the subject to perceive the display object but insufficient time to perform a catch-up saccadic movement to the object (generally greater than 40 milliseconds and less than 100 milliseconds and, in accordance with one embodiment, for approximately 75 milliseconds), causing the display object to abruptly appear at a predetermined location relative to the center marker, and then determining the maximum distance from the central marker during which the subject can correctly identify the object during a minimum three of five consecutive trials. As one example, the display object size is twice the size of the smallest object correctly identified during the static visual acuity test. Additional maximum distances can be calculated for display objects placed in various directions from the central marker; for examples, to the right, left, above, and below. In another embodiment of the invention, the object appearance distance from the central marker is maintained fixed, and the duration of the presentation is reduced until the subject fails to correctly identify the object during a minimum three of five consecutive trials.

The static assessment and any two from among the four dynamic measurements are then used, in process 204 to determine an impairment of the subject's gaze stabilization system. The relative extent to which impairments in the VOR, smooth pursuit, saccadic, and optokinetic systems each reduce an subject's ability to accurately perceive display objects when either or both of the subject or the display object is in motion is determined by comparing results of among any three or all four dynamic acuity measures; including, head moving/object fixed, head fixed/object continuously moving, head fixed/object discontinuously moving, and head fixed/object continuously moving with a patterned large field background. One method for comparing an individual dynamic measure with a static acuity measure is to calculate, for that dynamic condition, the ratio between the dynamic and static acuity measures. A second method would be to calculate the acuity differences between the dynamic measure and the static measure. A third method would be to calculate differences or ratios among two or more of the dynamic acuity measures.

Figure 3:
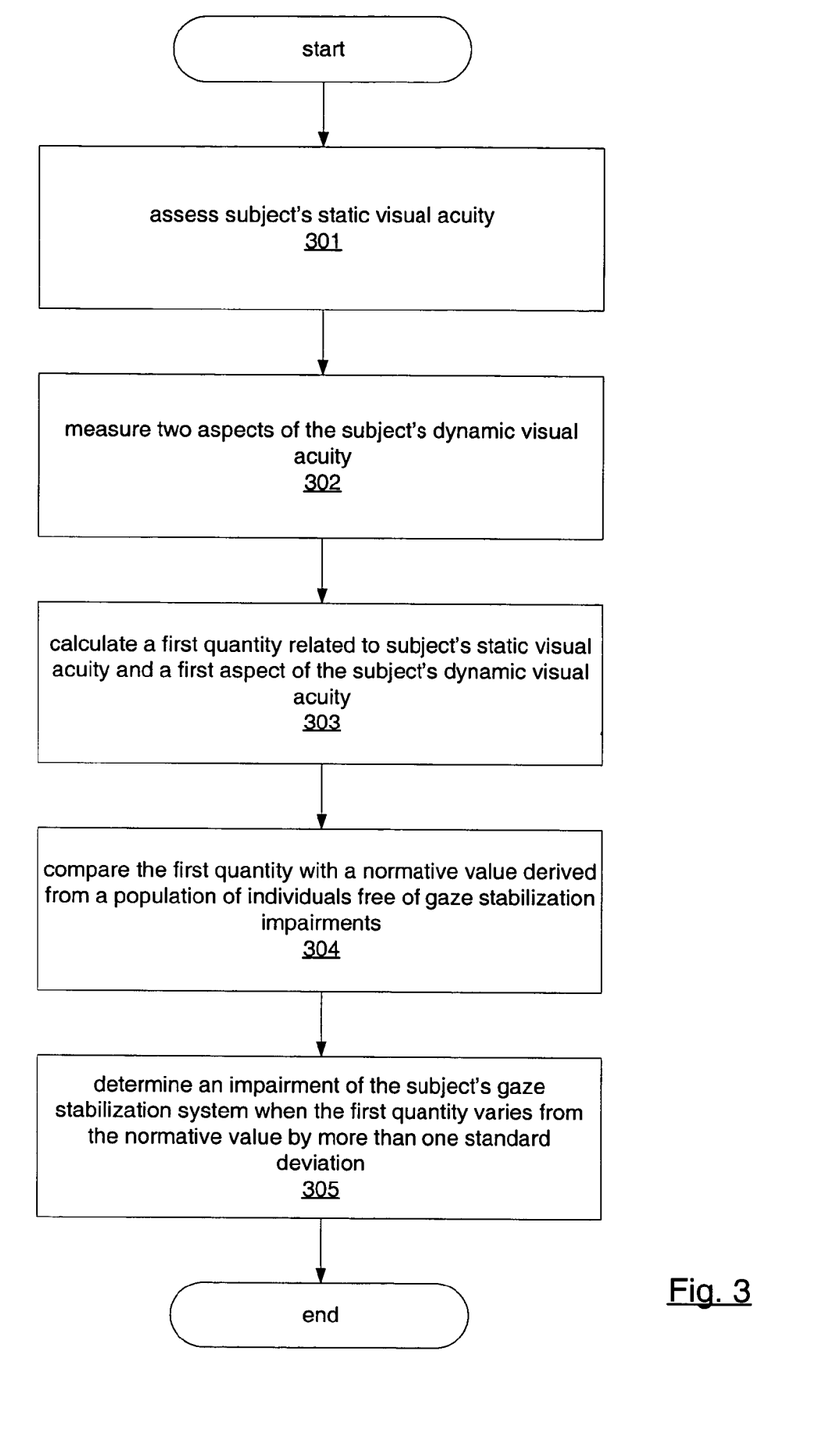
FIG. 3 is flow chart illustrating a method for isolating and quantifying impairments of a subject's gaze stabilization system employing a test population free of medical problems in accordance with a further embodiment of the invention.

FIG. 3 is flow chart illustrating a method for isolating and quantifying impairments of a subject's gaze stabilization system employing a test population free of medical problems in accordance with a further embodiment of the invention. In process 301, the subject's static visual acuity is assessed as described with respect to FIG. 2. At least two aspects of the subject's dynamic visual acuity are then measured 302 (such as two of: measuring the subject's visual acuity when his or her head is moving and a display object is fixed, measuring the subject's visual acuity when his or her head is fixed and a display object is moving, measuring the subject's visual acuity when the subject's head is fixed and a display object is discontinuously moving, or measuring the subject's visual acuity when the subject's head is fixed and a display object and/or patterned large field background is moving continuously or discontinuously). A first quantity related to both the subject's static visual acuity and a first aspect of the subject's dynamic visual acuity is calculated in process 303 and the first quantity is compared, in process 304 with a normative value similarly derived from a population of subjects free of gaze stabilization impairments. An impairment of the subject's gaze stabilization system is determined 305 when the first quantity varies from the normative value by more than one standard deviation.

For example, results of the head moving/object fixed, head fixed/object continuously moving, head fixed/object discontinuously moving, and/or head fixed/object and patterned large field background moving continuously processes described above may be obtained by testing a population of individuals determined to be free of medical problems impacting the functioning of systems controlling their gaze stabilization. Statistical methods described in the prior art may be used to establish normal ranges of results for subjects grouped by age. Statistical quantities for establishing normal ranges may include but are not limited to age-matched population averages, medians, standard deviations, and standard errors. Impairments can then be differentiated and quantified in individuals suspected of having problems with gaze stabilization. This is accomplished by obtaining the head moving/object fixed, head fixed/object continuously moving, head fixed/object discontinuously moving, and head fixed/object and patterned large field background continuously moving results of the subject with suspected problems, and comparing the suspect subject's results with those of the appropriate age-matched normal range. One or more statistical quantities may then used to determine the extent and characteristics of impairments of subject's gaze stabilization. Such statistical comparisons may include but are not limited to a measurement quantity being considered abnormal that differs by more than one standard deviation from the age-matched normal range average value obtained for that quantity.

Similarly, results of the head moving/object fixed, head fixed/object continuously moving, head fixed/object discontinuously moving, and/or head fixed/object and patterned large field background moving processes described above may be obtained by testing populations of individuals that are known to successfully perform specified work and sports related activities in their daily lives, such activities including but not limited to flying an aircraft, operating a heavy piece of machinery that moves, playing football, basketball, or tennis. Minimum performance ranges of results grouped by specified work and sports related activities may be established for the described measures using statistical methods described in the prior art. Statistical quantities may include but are not limited to population averages, medians, standard deviations, and standard errors. Limitations in gaze stabilization can then be differentiated and quantified in individuals suspected of having gaze stabilization problems that may compromise their ability to perform the similar work and sports related activities safely and effectively. This goal is accomplished by obtaining the head moving/object fixed, head fixed/object continuously moving, head fixed/object discontinuously moving, and head fixed/object and patterned large field background continuously moving results of the subject with suspected performance limitations, and comparing this subject's results with those obtained from the population of individuals that are known to safely and effectively perform the same work or sports related activity. One or more statistical quantities are then used to determine the extent and characteristics of any performance limitations in subject's gaze stabilization. Such statistical comparisons may include but are not limited to a measurement quantity being considered abnormal when its value differs from the population average value obtained for that quantity by one or more standard deviations.

Further, specified work and sports related activities may be analyzed theoretically to determine the maximum velocities and directions of head and visual object movements, and the types and motions of large field backgrounds. The activities may be further analyzed to determine the minimum acceptable visual acuity requirements. These theoretical values are then used to derive, for each work and sports activity, minimum performance standards for each of the head moving/object fixed, head fixed/object moving continuously, head fixed object moving discontinuously, and head fixed/object and patterned large field background continuously moving tests.

Figure 4:
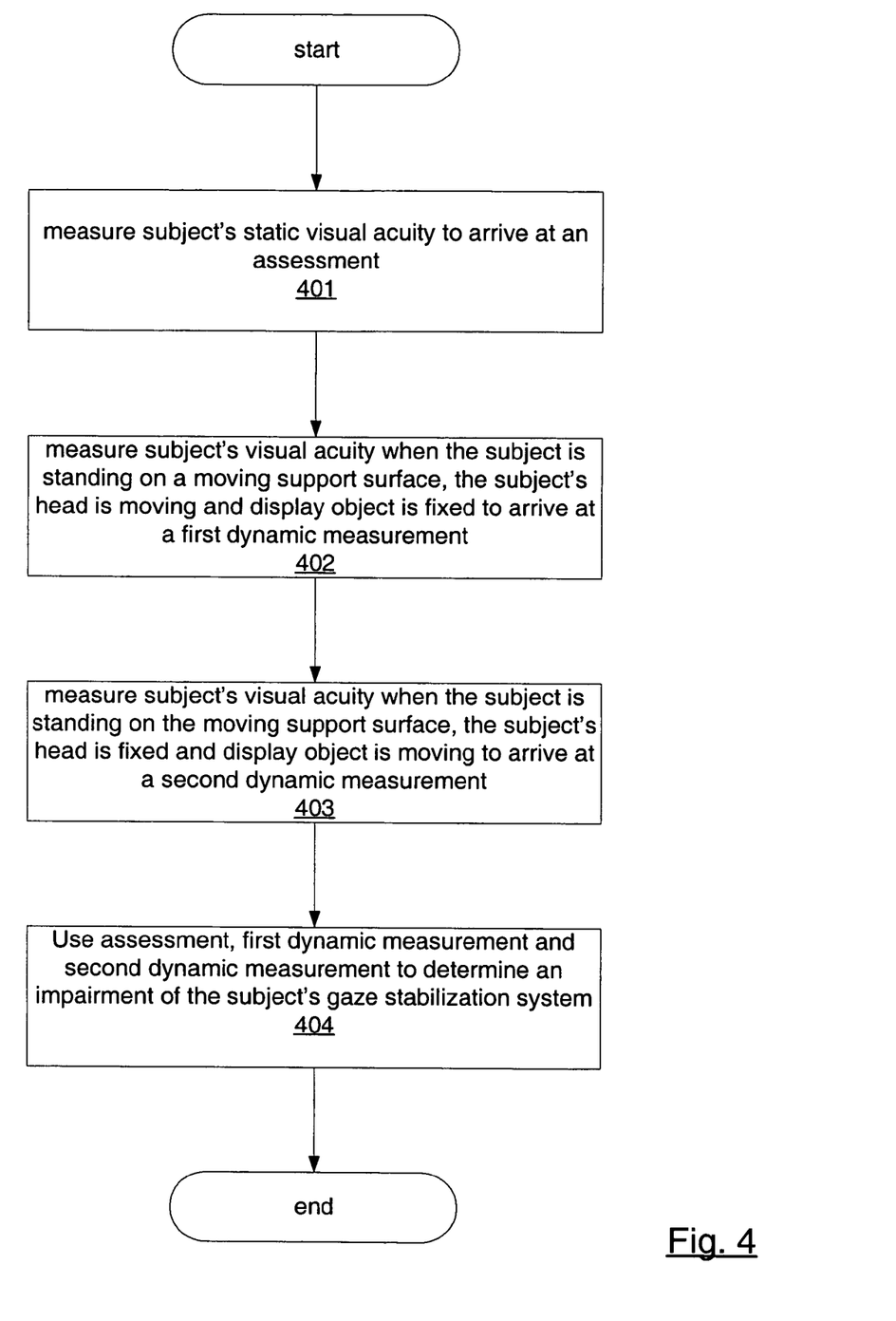
FIG. 4 is a flow chart illustrating a method for isolating and quantifying impairments of a subject's gaze stabilization system employing a free standing balancing task in accordance with another embodiment of the invention.

Methods and devices described above may be combined with additional methods and devices in which the subject performs one or more visual acuity tests while at the same time performing a specified free standing balance or walking task. FIG. 4 is a flow chart illustrating a method for isolating and quantifying impairments of a subject's gaze stabilization system employing a free standing balancing task in accordance with another embodiment of the invention. In accordance with this embodiment, the subject's static visual acuity is measured 401 to arrive at an assessment. The subject is directed 402 to perform at least one free standing balance task while measuring the subject's visual acuity. The free standing balance task may include standing on at least one surface which moves (either with constant velocity or with acceleration) in relation to display of the display object, for example a treadmill. In process 403, the subject's visual acuity is measured when the subject's head is moving and a display object is fixed to arrive at a first dynamic measurement. The subject's visual acuity is then measured 404 when the subject's head is fixed and the display object is moving to arrive at a second dynamic measurement.

Other test combinations which may be employed with respect to processes 402-404 include the following:

1) While performing one or more gaze stabilization tests, the subject stands on a one or more support surface and/or is surrounded by one or more surfaces that are capable, under computer control, of being actively and independently moved about one or more axes. Sensing devices measure one or more quantities related to the motions of the standing subject, the measurement quantities are transmitted to a computer and the computer causes the one or more support and surrounding surfaces to move in functional relation to the subject's motions. In one embodiment, one or more compliant elements cause the surface to move passively about one or more axes in response to the contact forces exerted by the freely standing subject.

In combining gaze stabilization and freely standing balance tasks, one or more surfaces may be caused to commence continuous movement in temporal relation to presentation of the display object and the large field background. Initiating surface motions well in advance of the display object presentation provides sufficient time to coordinate postural and gaze stabilizing movements. Beginning surface motions, display object presentations, and large field background motions in close temporal relation, in contrast, provide little if any time for coordination of postural and gaze movements.

2) While performing one or more gaze stabilization tests, the subject stands on a support surface that is capable, under computer control, of being actively moved about one or more axes. In one embodiment, the support surface is caused to move abruptly in temporal relation to the presentation of the display object and the large field background. Again, initiating surface motions well in advance of the display object presentation with or without large field background motions provides sufficient time to coordinate postural and gaze stabilizing movements. Beginning the surface motions and display object presentations, with or without large field background motions, in close temporal relation, in contrast, provides the subject with little time for coordination of postural and gaze movements.

3) While performing one or more gaze stabilization tests, the subject walks on a treadmill. The treadmill belt may move continuously at a constant velocity or may be under active control of a computer. In accordance with one embodiment, the velocity of treadmill belt movement changes abruptly in temporal relation to the presentation time of the display object. The display object may or may not also include a moving large field background. Abrupt changes may include causing a fixed belt to begin moving, or causing the velocity of the moving belt either change abruptly or to cease moving. Changes in treadmill belt motions initiated well in advance of the display object presentation provides the subject with sufficient time to coordinate gait and gaze stabilizing movements. Initiating changes in treadmill belt motion and display object presentations in close temporal relation, in contrast, provides the subject with little time for coordination of gait and gaze movements.

The assessment and the first and second dynamic measurements are then used to determine 405 an impairment of the subject's gaze stabilization system in accordance one or more of the methodologies described above.

While the invention has been described in connection with specific embodiments thereof, it will be understood that it is capable of further modification. This application is intended to cover any variation, uses, or adaptations of the invention and including such departures from the present disclosure as come within known or customary practice in the art to which invention pertains.

What is claimed is:

1. A method for isolating and quantifying impairments of a subject's gaze stabilization system, the method comprising:
   measuring the subject's static visual acuity to arrive at an assessment;
   measuring the subject's visual acuity when the subject's head is moving and a display object is fixed to arrive at a first dynamic measurement;
   measuring the subject's visual acuity when the subject's head is fixed and the display object is moving to arrive at a second dynamic measurement;
   using the assessment and the first and second dynamic measurements to determine an impairment of the subject's gaze stabilization system.

2. A method according to claim 1, wherein measuring the subject's static visual acuity to arrive at an assessment includes using the assessment to set parameters for a performance of a task by the subject.

3. A method according to claim 1, further comprising:
   measuring the subject's visual acuity when the subject's head is fixed and the display object is discontinuously moving to arrive at a third dynamic measurement; and
   using the assessment and the first, second and third dynamic measurement to determine impairment of the subject's gaze stabilization system.

4. A method according to claim 1, further comprising:
   measuring the subject's visual acuity when the subject's head is fixed, the display object is moving, and a patterned large field background is moving to arrive at a fourth dynamic measurement to determine impairment of the subject's gaze stabilization system.

5. A method according to claim 1, wherein assessing the subject's static visual acuity includes determining a smallest object that the subject can identify during a plurality of trials.

6. A method according to claim 1, wherein measuring the subject's visual acuity when the subject's head is moving and the display object is fixed includes:
   fixing the size of the display object in relation to the subject's static visual acuity;
   fixing the duration that the display object is displayed to between 40 and 100 milliseconds; and
   determining the maximum head movement velocity during which the subject can correctly identify the display object over a plurality of trials.

7. A method according to claim 1, wherein measuring the subject's visual acuity when the subject's head is fixed and the display object is continuously moving includes:
fixing the size of the display object in relation to the subject's static visual acuity; and fixing the duration that the display object is displayed to between 40 and 100 milliseconds; and
determining the maximum display object movement velocity during which the subject can correctly identify the display object over a plurality of trials.

8. A method according to either of claims 6 or 7, wherein the display object is displayed for approximately 75 milliseconds.

9. A method according to claim 1, wherein measuring the subject's visual acuity when the subject's head is fixed and the display object is continuously moving includes:
displaying a patterned large field background; and
moving the patterned large field background.

10. A method according to claim 3, wherein measuring the subject's visual acuity when the subject's head is fixed and the display object is discontinuously moving includes:
fixing the size of the display object in relation to the subject's static visual acuity;
fixing the duration that the display object is displayed to about 90 milliseconds;
causing the subject to direct gaze towards a central marker for between 40 and 100 milliseconds;
causing the display object to appear at a predetermined location relative to the central marker; and
determining the maximum distance from the central marker during which the subject can correctly identify the display object over a plurality of trials.

11. A method according to claim 10, wherein the subject is caused to direct gaze toward a central marker for approximately 75 milliseconds.

12. A method according to claim 10, wherein causing the display object to appear at a predetermined location relative to the central marker includes causing the display object to appear at a fixed distance from the central marker.

13. A method according to claim 10, wherein causing the display object to appear at a predetermined location relative to the central marker includes causing the display object to appear at various directions from the central marker.

14. A method according to claim 1, wherein measuring the subject's static visual acuity includes using a Snellen eye chart.

15. A method according to claim 1, wherein measuring the subject's static visual acuity includes using a Tumpling E chart.

16. A method according to claim 1, further comprising:
directing the subject to perform at least one free standing balance task while measuring the subject's visual acuity.

17. A method according to claim 16, wherein directing the subject to perform at least one free standing balance task includes directing the subject to stand on at least one surface which moves in relation to display of the display object.

18. A method according to claim 17, further comprising:
moving a patterned large field background in relation to the movement of the surface.

19. A method according to claim 17, wherein the surface moves discontinuously in relation to display of the display object.

20. A method according to any of claims 16, 17, or 18, wherein the surface is a force plate.

21. A method according to any of claims 16, 17 or 18, wherein the surface is a treadmill.

22. A method according to claim 21, wherein velocity associated with the treadmill is constant.

23. A method according to claim 21, wherein velocity associated with the treadmill is caused to vary.

24. A method according to claim 16, 17 or 18, wherein directing the subject to perform at least one free standing balance task includes directing the subject to perform at least one free standing balance task while surrounded by a visual surround.

25. A method for isolating and quantifying impairments of a subject's gaze stabilization system, the method comprising:
assessing the subject's static visual acuity;
measuring at least two aspects of the subject's dynamic visual acuity;
calculating a first quantity related to both the subject's static visual acuity and a first aspect of the subject's dynamic visual acuity;
comparing the first quantity with a normative value similarly derived from a population of individuals free of gaze stabilization impairments; and
and determining an impairment of the subject's gaze stabilization system when the first quantity varies from the normative value by more than one standard deviation.

26. A method according to either of claims 14 or 15, wherein measuring aspects of the subject's dynamic visual acuity includes measuring aspects of the subject's dynamic visual acuity related to two or more of:
the subject's vestibule-ocular reflex system;
the subject's smooth pursuit eye movement system;
the subject's optokinetic eye movement system; and
the subject's saccadic movement system.

27. A method according to claim 26, further comprising:
calculating a second quantity related to the subject's static visual acuity and a second aspect of the subject's dynamic visual acuity;
comparing the second quantity with a normative value similarly derived from a population of individuals free of gaze stabilization impairments; and
determining a second impairment of the subject's gaze stabilization system when the third quantity varies from the normative value by more than one standard deviation.

28. A method for isolating and quantifying impairments of a subject's gaze stabilization system, the method comprising:
assessing the subject's static visual acuity;
measuring the subject's visual acuity when the subject's head is moving and a display object is fixed to determine a first relationship to the subject's static visual acuity;
measuring the subject's visual acuity when the subject's head is fixed and the display object is continuously moving to determine a second relationship to the subject's static visual acuity;
measuring the subject's visual acuity when the subject's head is fixed and the display object is discontinuously moving to determine a third relationship to subject's static visual acuity;
measuring the subject's visual acuity when the subject's head is fixed, the display object is continuously moving, and the patterned large field background is continuously moving to determine a fourth relationship to the subject's static visual acuity; and determining the extent to which impairments of the subject's gaze stabilization system reduce the subject's ability to perceive objects based on the first, second, third, and fourth relationships.

29. A method for isolating and quantifying impairments of a subject's gaze stabilization system, the method comprising:

measuring the subject's static visual acuity to arrive at an assessment;

measuring the subject's visual acuity when the subject is standing on a continuously moving support surface, the subject's head is moving a display object is fixed to arrive at a first dynamic measurement;

measuring the subject's visual acuity when the subjects is standing on the continuously moving support surface, the subject's head is fixed and the display object is moving to arrive at a second dynamic measurement;

using the assessment and the first and second dynamic measurements to determine an impairment of the subject's gaze stabilization system.

30. A method for isolating and quantifying impairments of a subject's gaze stabilization system, the method comprising:

measuring the subject's static visual acuity to arrive at an assessment;

measuring the subject's visual acuity when the subject is standing on a support surface that is discontinuously moving, the subject's head is moving a display object is fixed to arrive at a first dynamic measurement;

measuring the subject's visual acuity when the subjects is standing on the support surface that is discontinuously moving, the subject's head is fixed and the display object is moving to arrive at a second dynamic measurement;

using the assessment and the first and second dynamic measurements to determine an impairment of the subject's gaze stabilization system.

\* \* \* \* \*